(12) United States Patent
Scofield et al.

(10) Patent No.: US 9,940,836 B2
(45) Date of Patent: Apr. 10, 2018

(54) ESTIMATING TRANSIT QUEUE VOLUME USING PROBE RATIOS

(71) Applicant: INRIX INC., Kirkland, WA (US)

(72) Inventors: Christopher L. Scofield, Seattle, WA (US); Dominic Jordan, Manchester (GB)

(73) Assignee: INRIX, INC., Kirkland, WA (US)

( * ) Notice: Subject to any disclaimer, the term of this patent is extended or adjusted under 35 U.S.C. 154(b) by 0 days.

(21) Appl. No.: 15/123,043

(22) PCT Filed: Mar. 3, 2015

(86) PCT No.: PCT/US2015/018544
§ 371 (c)(1),
(2) Date: Sep. 1, 2016

(87) PCT Pub. No.: WO2015/134542
PCT Pub. Date: Sep. 11, 2015

(65) Prior Publication Data
US 2017/0076596 A1    Mar. 16, 2017

Related U.S. Application Data

(60) Provisional application No. 61/946,962, filed on Mar. 3, 2014.

(51) Int. Cl.
G08B 21/00        (2006.01)
G08G 1/0967      (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC .............. G08G 1/0129; G08G 1/0141; G08G 1/096791; H04W 4/046
(Continued)

(56) References Cited

U.S. PATENT DOCUMENTS

2002/0082767 A1    6/2002  Mintz
2008/0204277 A1    8/2008  Sumner
(Continued)

OTHER PUBLICATIONS

Corresponding International Application No. PCT/US15/18544, International Search report and written opinion dated Jun. 25, 2015.
(Continued)

*Primary Examiner* — Mark Rushing
(74) *Attorney, Agent, or Firm* — Cooper Legal Group, LLC

(57) ABSTRACT

Transit through an area by a population of travelers may be evaluated by a number of techniques, and may be useful for routing, transit time estimation, and transit control. Some techniques involve the use of probes, such as individuals or vehicles that are tagged and trackable through the area. However, estimating properties such as transit queue volume through probe counts may be difficult, as the ratio of probes to the overall population may vary. Presented herein are techniques for estimating transit properties by evaluating transit queues to estimate the probe ratio for an area. Such techniques involve counting and tracking the probes in a transit queue to estimate a queue length change of the transit queue, and a probe rate change of probes entering and exiting the transit queue. This information may inform estimates of the probe ratio, and in turn regional transit estimates, such as transit queue volumes.

20 Claims, 9 Drawing Sheets

(51) Int. Cl.
| | |
|---|---|
| G06N 99/00 | (2010.01) |
| G08G 1/01 | (2006.01) |
| G08G 1/0968 | (2006.01) |
| B60W 30/14 | (2006.01) |
| G05D 1/00 | (2006.01) |
| G07C 5/00 | (2006.01) |
| G08G 1/0965 | (2006.01) |
| A61B 5/0205 | (2006.01) |
| A61B 5/0476 | (2006.01) |
| A61B 5/00 | (2006.01) |
| G01C 21/34 | (2006.01) |
| G05D 1/02 | (2006.01) |
| H04B 1/3822 | (2015.01) |
| H04L 29/08 | (2006.01) |
| B64C 39/02 | (2006.01) |
| G08G 1/097 | (2006.01) |
| H04B 7/185 | (2006.01) |
| G06F 17/30 | (2006.01) |
| G06Q 20/10 | (2012.01) |
| G06Q 30/02 | (2012.01) |
| G08G 1/07 | (2006.01) |
| H04W 4/00 | (2018.01) |
| H04W 12/08 | (2009.01) |
| H04M 15/00 | (2006.01) |
| G06Q 40/08 | (2012.01) |
| H04L 9/32 | (2006.01) |
| B60R 16/023 | (2006.01) |
| G07B 15/00 | (2011.01) |
| G08G 1/0962 | (2006.01) |
| H04W 4/04 | (2009.01) |
| A61B 5/024 | (2006.01) |
| A61B 5/053 | (2006.01) |
| G06Q 50/30 | (2012.01) |
| G08G 1/065 | (2006.01) |

(52) U.S. Cl.
CPC ........ *A61B 5/4845* (2013.01); *B60R 16/0236* (2013.01); *B60W 30/143* (2013.01); *B64C 39/024* (2013.01); *G01C 21/3415* (2013.01); *G01C 21/3469* (2013.01); *G05D 1/0011* (2013.01); *G05D 1/0088* (2013.01); *G05D 1/021* (2013.01); *G06F 17/30241* (2013.01); *G06N 99/005* (2013.01); *G06Q 20/102* (2013.01); *G06Q 30/0283* (2013.01); *G06Q 40/08* (2013.01); *G07B 15/00* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/07* (2013.01); *G08G 1/097* (2013.01); *G08G 1/0962* (2013.01); *G08G 1/0965* (2013.01); *G08G 1/0967* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/001* (2013.01); *H04W 4/046* (2013.01); *H04W 12/08* (2013.01); *A61B 5/024* (2013.01); *A61B 5/0531* (2013.01); *B60W 2710/1044* (2013.01); *B60W 2710/18* (2013.01); *B60W 2720/10* (2013.01); *B64C 2201/123* (2013.01); *G06Q 50/30* (2013.01); *G06Q 2240/00* (2013.01); *G08G 1/065* (2013.01)

(58) Field of Classification Search
USPC .......................................... 340/934
See application file for complete search history.

(56) References Cited

U.S. PATENT DOCUMENTS

| 2009/0271100 | A1 | 10/2009 | Kim et al. | |
|---|---|---|---|---|
| 2013/0041573 | A1* | 2/2013 | Ochi ................... | G01S 13/345 701/117 |
| 2015/0120175 | A1* | 4/2015 | Vahidi ................. | G08G 1/0141 701/119 |

OTHER PUBLICATIONS

EP Search Report cited in EP Application No. 15758334.5 dated Nov. 7, 2017, 7 pgs.

* cited by examiner

ESTIMATING TRANSIT QUEUE VOLUME USING PROBE RATIOS

CROSS-REFERENCE TO RELATED APPLICATIONS

The present application claims priority under 35 U.S.C. § 119(e) to U.S. Patent Application No. 61/946,962, filed on Mar. 3, 2014, the entirety of which is incorporated by reference as if fully rewritten herein.

BACKGROUND

Within the field of computing, many scenarios involve the transit of travelers through an area, such as individuals who are walking or driving a vehicle such as a car through a road network of a city. A transit agency, such as a branch of a regional government may be responsible for monitoring the transit of such travelers, and for setting policy, managing resources, and operating transit control devices, such as traffic lights, in order to alleviate traffic congestion, promote safety, and to address problems that interfere with the transit of such travelers through the region.

In such scenarios, determination of transit queue volumes, such as an evaluation of a road network of a city to determine the existence of traffic congestion. Devices may utilize such information, e.g., for estimating a travel time along a route; for choosing among several possible routes to a destination; and/or for adjusting transit controls to alleviate traffic congestion in an area.

Many techniques may be utilized to estimate transit queue volume in an area, such as human observation; tagging and tracking of individual travelers; and cameras or other detectors positioned throughout the area. However, such techniques may involve significant costs in terms of equipment purchase, deployment, monitoring, and maintenance, and may also exhibit insufficient accuracy and/or timeliness in the collected data about transit queue volume. Additionally, data about the volume and fluctuation of transit queues in various areas may not be attainable in a reliable and rapid manner using such techniques, which may limit the accuracy and responsiveness of transit control measures.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One set of techniques for estimating transit queue volumes involves the use of probes, e.g., individuals or vehicles that are tracked during travel through an area. The number and travel patterns of such probes may enable the determination of many details about transit through an area, including transit queue volumes. However, the accuracy of such estimation may be diminished by incomplete or inaccurate data about how representative the probes may be of a particular area. As a first such example, if six probes are present in an area, such probes may represent 600 travelers if the probe ratio is 100:1, and 6,000 travelers if the probe ratio is 1,000:1. As a second such example, the probe ratio may change over time and by region; e.g., the ratio of probes present in a first area may differ from the number of probes present in a second area. It may therefore be difficult to evaluate the volume or depth of a transit queue based on a count of the probes located in the transit queue, because the ratio of such probes may be difficult to determine.

Presented herein are techniques for estimating transit through an area based on a number of probes that are present among the population of travelers. Such techniques involve monitoring a probe speed of respective probes in the area to detect a transit queue. From the probe speeds of the probes, estimates may be derived of the queue length change of the transit queue, and a probe rate change of probes in the transit queue. From the queue length change and the probe rate change, a probe ratio among travelers of the transit queue may be identified; and using the count of the probes and the probe ratio, the transit volume of the transit queue may be identified. Such techniques may inform various estimates of transit volumes through the area consistent through the detection of probe vehicles in accordance with the techniques presented herein.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
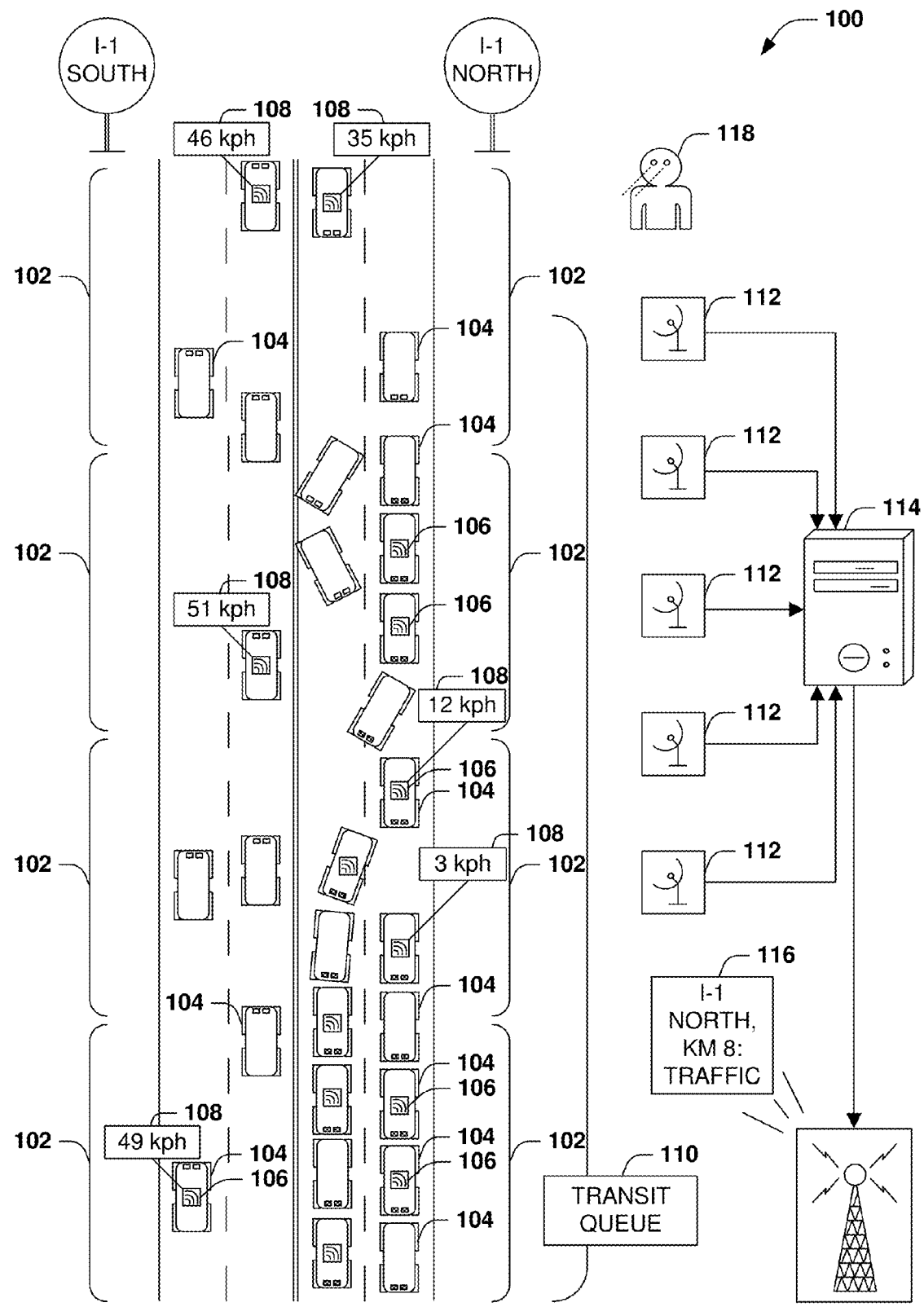
FIG. 1 is an illustration of an example scenario featuring an estimation of transit volume of travelers in an area.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Introduction

FIG. 1 is an illustration of an example scenario 100 featuring techniques for estimating transit volume in an area 102, such as a particular segment of a regional road network. In this example scenario 100, a set of travelers 104 in the area 102 (particularly vehicles traveling on the road) are caught in a transit queue 110, involving a high density of slow-moving travelers 104, while other travelers 104 are freely traveling through the area 102. Estimates of transit volume in respective areas 102 may be useful, e.g., for adjusting routing and estimated travel times, and also for enabling a transit service to adjust transit control mechanisms, such as tolls and traffic signals.

To this end, many techniques may be utilized to estimate transit volume in various areas 102 of a region. As a first example, vehicles may be monitored by monitoring equipment 112, such as roadside cameras and/or road-embedded pressure sensors, that report to a transit service 114. A notification 116 of transit volume may be broadcast 116 through the area 102, e.g., in order to advise travelers 104 of the development, locations, and/or severity of transit volume in various areas 102. As a second example, probes 106 may be deployed within the population of vehicles 104, such as selected vehicles that transmit telemetrics, such as location, speed, and acceleration, to the transit service 114, which may extrapolate transit volume from the distribution of probes 106 through the areas 102. As a third such example, an individual 118, such as transit service personnel, may visually evaluate the area 102 and estimate transit volume of travelers 104 therethrough.

Although such techniques may enable the estimation of traveler volume, several disadvantages may arrive therefrom. As a first such example, these methods may entail significant expense in terms of equipment (e.g., implementing hundreds of fixed roadside and road-embedded sensors may entail significant costs for equipment acquisition, deployment, operation, monitoring, and maintenance), and the use of individuals may entail a disproportionately large hourly cost. As a second such example, these methods may be prone to error; e.g., an individual 118 may generate inaccurate and disproportionate estimates, and a first estimate by a first individual of an area 102 may conflict with a second estimate by a second individual for the same area 102. Monitoring equipment 112 may exhibit inaccuracy (e.g., the roadside camera may be partially obstructed by debris or weather elements, and pressure-sensitive equipment may count an 18-wheel vehicle several times while failing to count lighter vehicles such as motorcycles), and a transit service 114 that utilizes such equipment may produce incorrect traveler volume estimates. As a third such example, these techniques may provide traveler volume data in a delayed manner; e.g., a portion of a transit service 114 deployed in a remote area may not have a direct connection with a transit monitoring station, and may only report data sporadically, only in lengthy intervals, or only when visited by transit control personnel to retrieve the data. Therefore, the collection of such data may be suitable for surveying or historical study, but may be too slow for transit control management. As a fourth such example, such equipment methods may be fixed at a particular area 102, and traveler volume information about other areas 102 within a region may involve additional equipment costs, costly and time-consuming redeployment of existing equipment, and/or a significant delay to implement.

More particularly, the use of probes 106 to estimate transit volume may be difficult to extrapolate to transit volume throughout a region. These and other disadvantages may arise from the estimation of traveler volume using the techniques depicted in the example scenario 100 of FIG. 1. As a first such example, it may be difficult to translate a detected count of probes 106 in an area 102 with the general population of travelers 104 in the area 102, because the probe ratio of probes 106 to travelers 104 may vary. For example, in a first area 102, probes 106 may be prevalent and may exhibit a low ratio (e.g., a 100:1 ratio of travelers 104 to probes 106); while in a second area 102, probes 106 may be less prevalent as a proportion of the population of travelers 104, and may exhibit a high probe ratio (e.g., a 1100:1 ratio of travelers 104 to probes 106). As a second such example, the probe ratio may vary between a first area 102 and a second area 102, and a significant variance, such as a large standard deviation, may lead to significant inaccuracy in attributing a selected probe ratio to an entire region. Accordingly, it may be desirable to develop specific techniques for estimating transit volume in various areas not only using information about the locations and concentration of probes 106, but also by carefully estimating the probe ratio to achieve an accurate representation of the population of travelers 104 in the area 102.

B. Presented Techniques

Figure 2:
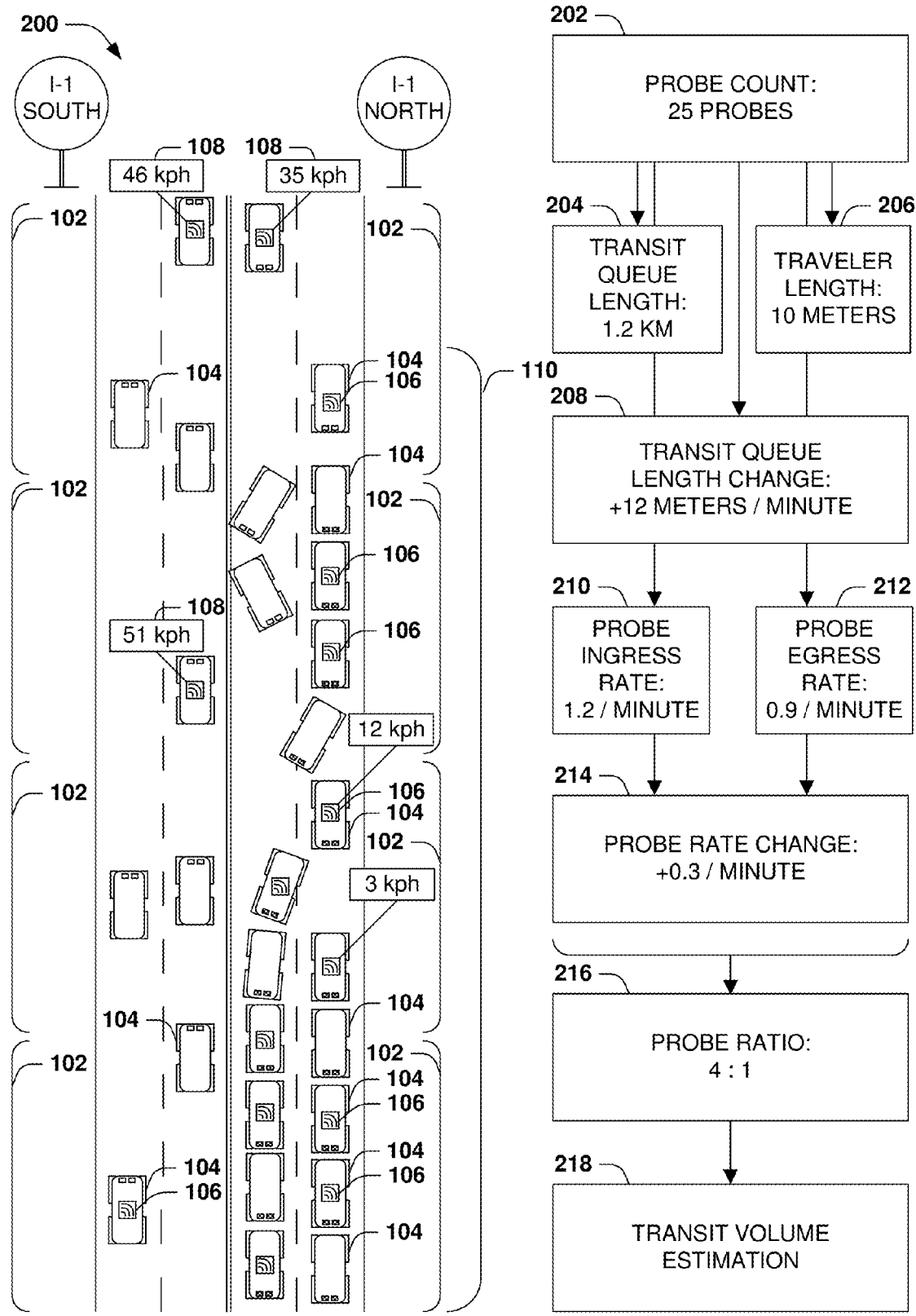
FIG. 2 is an illustration of an example scenario featuring an estimation of transit volume of travelers in an area in accordance with the techniques presented herein.

FIG. 2 is an illustration of an example scenario 200 featuring techniques for estimating transit volume in an area 102 in accordance with the techniques presented herein.

In this example scenario 200, in order to monitor transit volume in an area 102, a set of probes 106 is deployed within a population of travelers 104 to report such metrics as location and speed. Using this information, an estimation of transit volume 218 in the area 102 may be achieved in the following manner. A count 202 of probes in the area 102 is first identified (e.g., simply by comparing, among all reporting probes 106, the global positioning system (GPS) coordinates reported by the respective probes 106 with the coordinates defining the boundaries of the area 102). Based on such information, probe speeds of respective probes 108 may be evaluated to detect the presence of a transit queue 110, e.g., an area 102 in which transit speeds are reduced or stopped, and/or in which traveler density is high. From the probe speeds of the probes 106, transit queue length 204 may be determined (e.g., the length between an apparent starting point of the transit queue 110 where transit speeds of probes 106 are reduced, and an ending point of the transit queue 110 when transit speeds of probes 106 are restored to typical speeds). An estimate may also be performed of traveler length 206, e.g., the length consumed by an average traveler 104 or average probe 106 within the transit queue 110. Additionally, a transit queue length change 208 of the transit queue 110 may be estimated, e.g., the rate at which the transit queue 110 is extending or contracting. Together, an estimate of the transit queue length change 208 at which the transit queue 110 is expanding or contracting, coupled with an estimate of the traveler length 206, may indicate the number of travelers 104 entering and/or leaving the transit queue 110 over time. Also, estimates of the probe ingress rate 210 into the transit queue 110 and the probe egress rate 212 from the transit queue 110 may be performed. According to this information, a probe rate change 214 of probes 106 in the transit queue 110 may be determined. Comparing the transit queue length change 208, the traveler length 206, and the probe rate change 214 (e.g., the number of probes 106 entering and leaving the transit queue 110 over time, as compared with the number of travelers 104 entering and leaving the transit queue 110 over time) may enable an identification of a probe ratio 216, i.e., the degree to which the count of probes 106 is representative of a count of the travelers 104 in the area 102. The probe ratio 216 may then be used to estimate transit volume 218 in a variety of ways (e.g., as the overall number of travelers 104 present in the transit queue 110; the number of travelers 104 passing through the area 102; and/or the average transit delay of travelers 104 passing through the area 102), in accordance with the techniques presented herein.

C. Technical Effects

The techniques presented herein may provide a variety of technical effects in the scenarios provided herein.

As a first such example, the techniques provided herein may enable the collection of transit volume estimates 218 in a comparatively cost-effective manner as compared with other techniques, such as those illustrated in the example scenario 100 of FIG. 1. For example, the costs of deploying probes 106, such as installing devices in vehicles and/or deploying software to mobile devices such as mobile phones that are carried by travelers 104, are reasonably affordable due to rapid development of these areas of technology and an expansion of commercial offerings. Moreover, such equipment does not have to be developed for the specialized purpose of transit volume estimation 218 that raises the equipment costs, but may be acquired as general-purpose equipment and reconfigured for the task of estimating traveler volumes. Accordingly, the cost of deploying probes 106 throughout an area 102 may be significantly less than for portable equipment that is transported to the area 102 by transit service personnel.

As a second such example, the techniques provided herein may achieve more accurate transit volume estimation 218 than may be achieved by other techniques. For example, other techniques for estimating probe ratios 216 may be significantly inaccurate for a variety of reasons, and may lead to significant error in transit volume estimation 218. Additionally, the volume of probes 106 that may be cost-effectively deployed to an area 102 may provide some tolerance for equipment failures; e.g., the loss of data from a few probes 106 may little or no impact on probe estimation, whereas the loss of a single roadside camera may reduce or prevent transit volume estimation 218 for an entire area 102.

As a third such example, the techniques presented herein may enable a more rapid and flexible collection of transit volume estimates 218 than may be achieved by other techniques. For example, equipment that is deployed to a remote area may not be continuously connected to the transit service 114, such that data may be received from the equipment only sporadically, only over long intervals, and/or only when transit service personnel may visit the equipment to retrieve the data. These and other technical advantages may arise from transit volume estimation 218 in accordance with the techniques presented herein.

D. Example Embodiments

Figure 3:
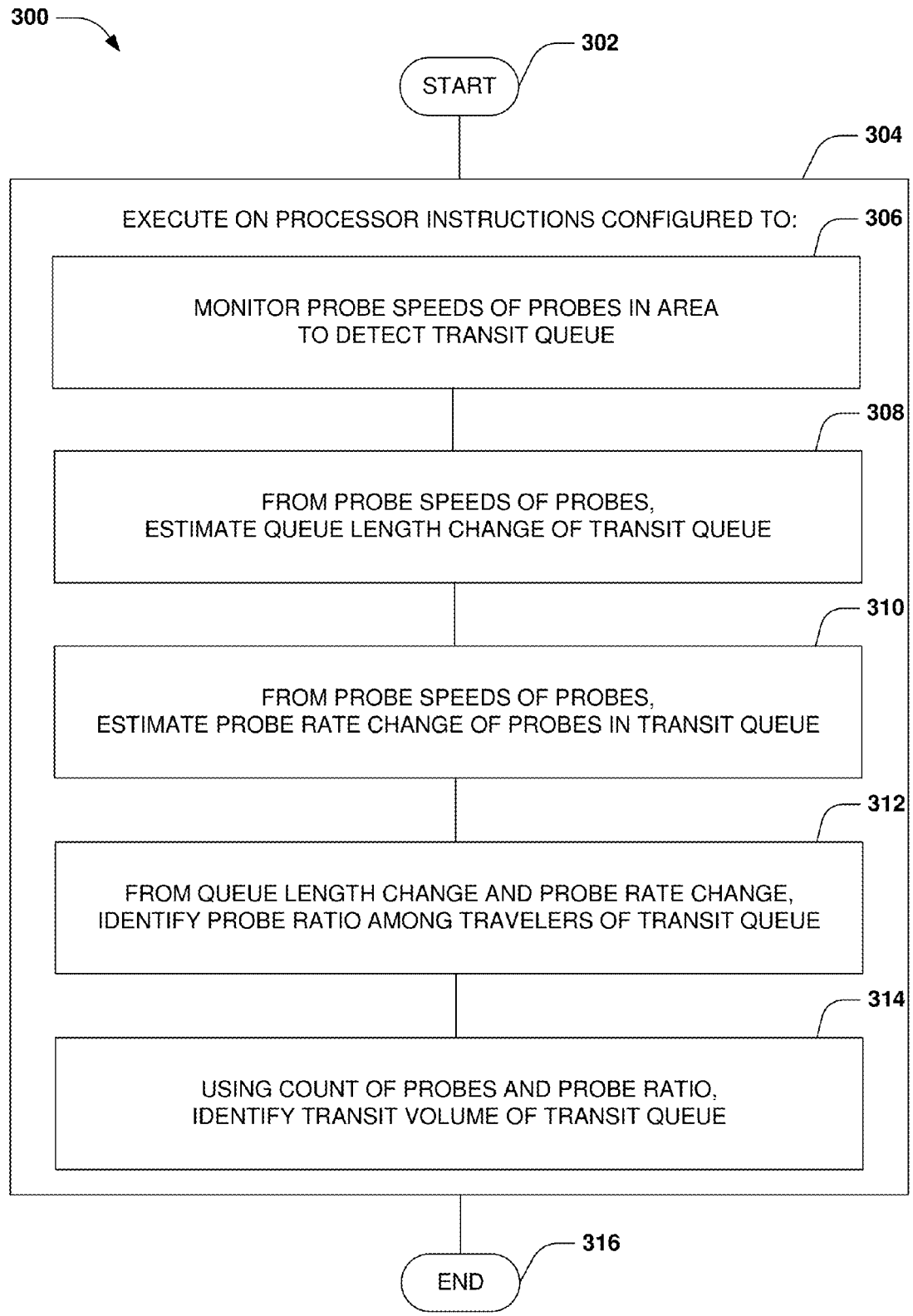
FIG. 3 is an illustration of an example method of estimating transit volume of travelers in an area, in accordance with the techniques presented herein.

FIG. 3 presents a first example embodiment of the techniques presented herein, illustrated as an example method 300 of estimating transit volume in an area 102. The example method 300 may be implemented on a device having a processor and access to data from probes 106 in an area 102. The example method 300 may be implemented, e.g., as a set of instructions stored in a memory component of the device (e.g., a memory circuit, a platter of a hard disk drive, a solid-state memory component, or a magnetic or optical disc) that, when executed by the processor of the device, cause the device to perform the techniques presented herein.

The example method 300 begins at 302 and involves executing 304 the instructions on the processor. Specifically, the instructions cause the device to monitor 306 a probe speed of respective probes 106 in the area 102 to detect a transit queue 110. The instructions also cause the device to, from the probe speeds of the probes 106, estimate 308 a queue length change 208 of the transit queue 110, and estimate 310 a probe rate change 212 of probes 106 in the transit queue. The instructions also cause the device to, from the queue length change 208 and the probe rate change 214, identify 312 a probe ratio 216 among travelers 104 of the transit queue 110. The instructions also cause the device to, using a count of the probes 106 and the probe ratio 216, identify 314 the transit volume of the transit queue 110. In this manner, the example method 300 enables the fulfillment of the location query 114 on behalf of the user 102 of the vehicle 104 in transit in accordance with the techniques presented herein, and so ends at 316.

Figure 4:
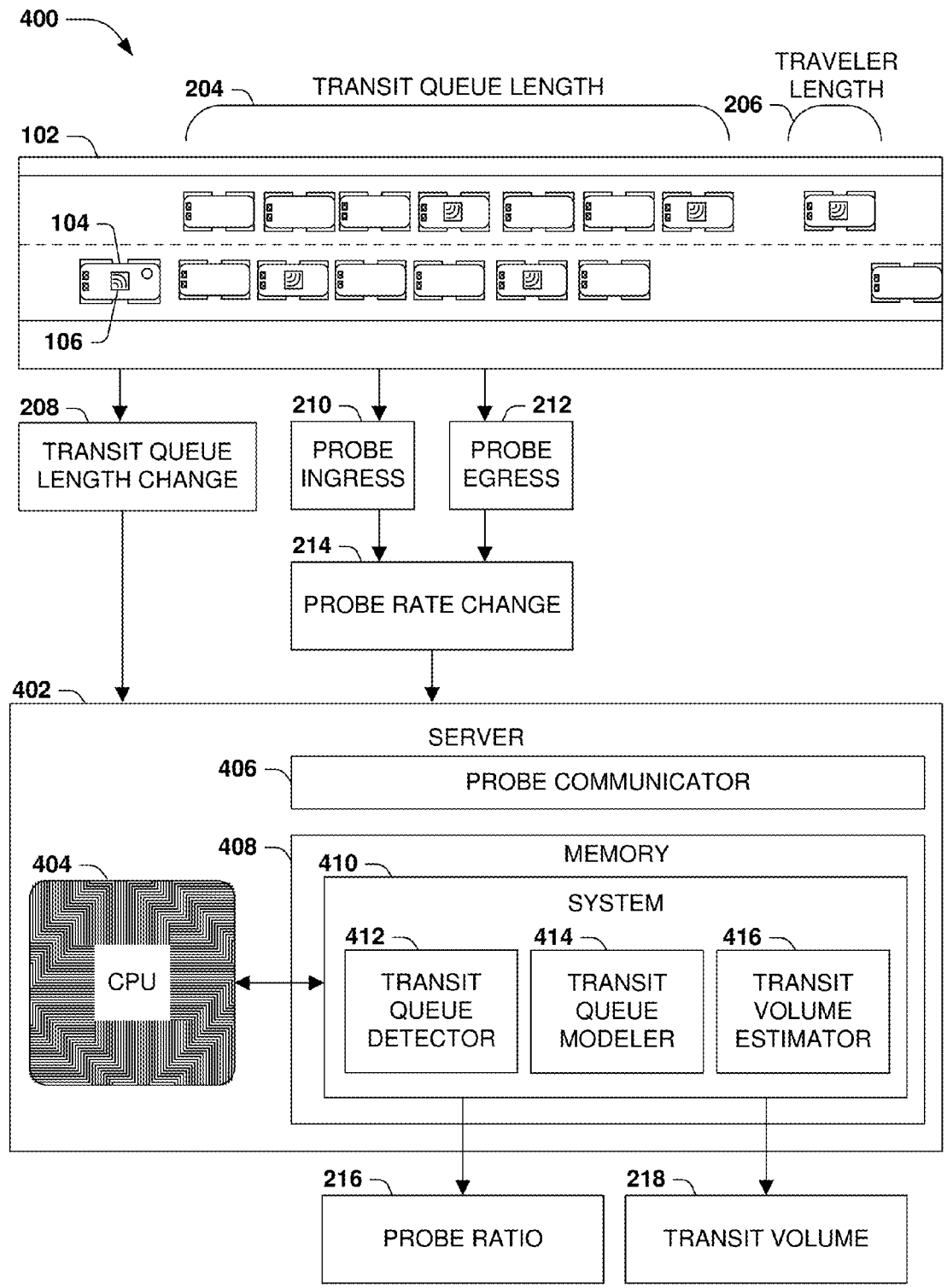
FIG. 4 is an illustration of a first example system for estimating transit volume of travelers in an area, in accordance with the techniques presented herein.

FIG. 4 presents an illustration of an example scenario 400 featuring a second example embodiment of the techniques presented herein, illustrated as an example server 402 comprising a system 410 that achieves a transit volume estimation 218 for an area 102. The example system 410 may be implemented, e.g., on a server 402 having a processor 404 and a probe 406 communicator that communicates with a navigation device within the probes 106 of the area 102 to receive data such as a probe speed. A portion of the server 402 may be located on a navigation device within one or more probes 106, and/or may be located at a remote location. Respective components of the example system 410 may be implemented, e.g., as a set of instructions stored in a memory 408 of the server 402 and executable on the processor 404 of the server 402, such that the interoperation of the components causes the server 402 to operate according to the techniques presented herein.

The example system 410 comprises a transit queue detector 412, which, from the probe speeds of the probes 106, identifies a transit queue 110. The example system 410 also comprises a transit queue modeler 414, which, from the probe speeds of the probes 106, estimates a queue length change 208 of the transit queue 110, and estimates a probe rate change 214 of the probes 106 in the transit queue 110. The example system 410 also comprises a transit volume estimator 416, which, from the queue length change 208 and the probe rate change 214, identifies a probe ratio 216 among travelers 104 of the transit queue 110; and, using a count of the probes 106 and the probe ratio 216, identifies the transit volume of the transit queue 110. In this manner, In this manner, the interoperation of the components of the example system 410 enables the server 402 to perform a transit volume estimation 218 of the area 102 in accordance with the techniques presented herein.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 5:
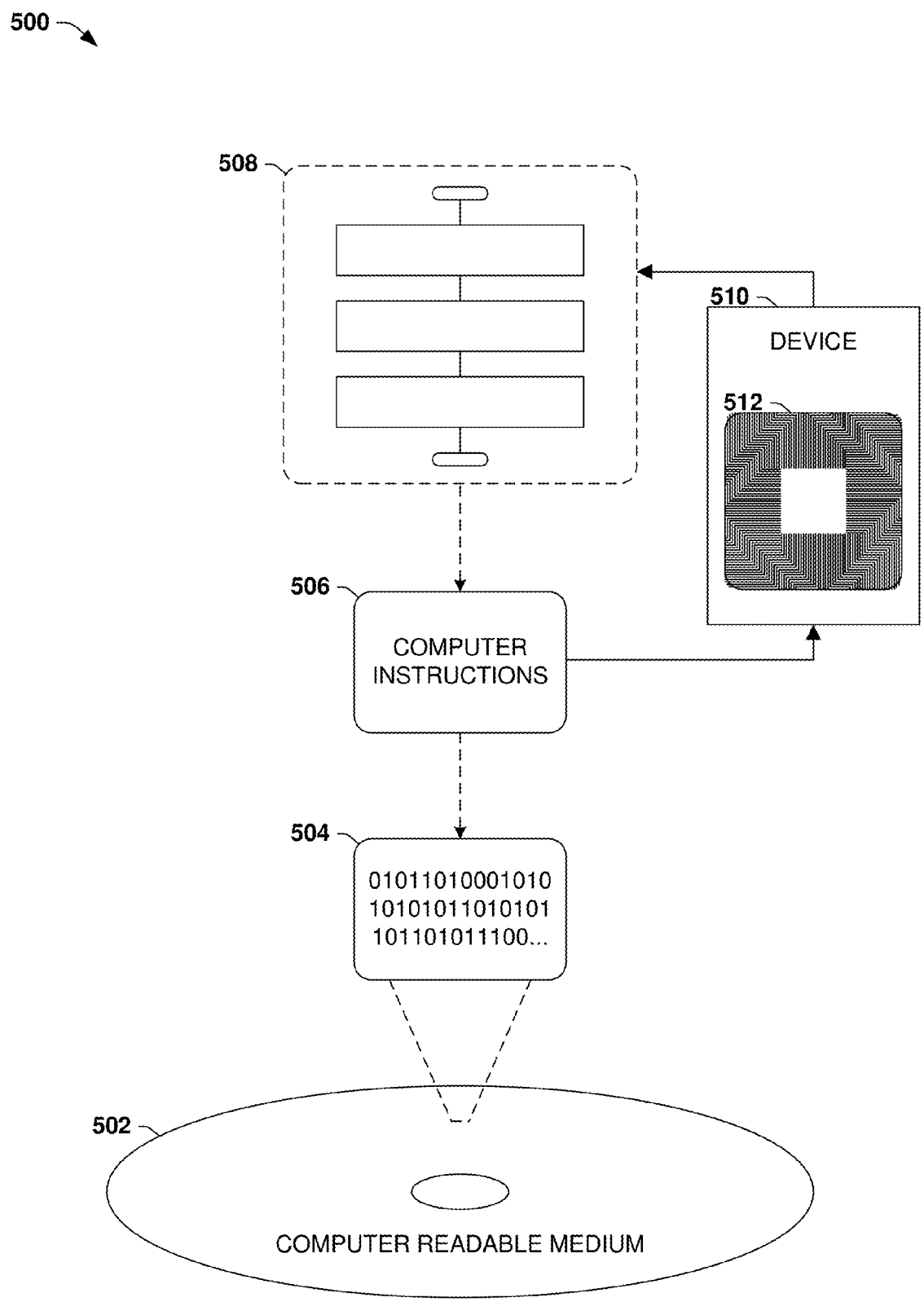
FIG. 5 is an illustration of an example computer-readable medium comprising processor-executable instructions configured to embody one or more of the provisions set forth herein.

An example computer-readable medium that may be devised in these ways is illustrated in FIG. 5, wherein the implementation 500 comprises a computer-readable medium 502 (e.g., a CD-R, DVD-R, or a platter of a hard disk drive), on which is encoded computer-readable data 504. This computer-readable data 504 in turn comprises a set of computer instructions 506 configured to operate according to the principles set forth herein. As a first such example, the computer instructions 506 may cause the device 510 to utilize a method of estimating transit volume in an area 102, such as the example method 300 of FIG. 3. As a second such example, the computer instructions 606 may provide a system for estimating transit volume in an area 102, such as the example system 410 in the example scenario 400 of FIG. 4. Many such computer-readable media may be devised by those of ordinary skill in the art that are configured to operate in accordance with the techniques presented herein.

E. Variable Aspects

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the example method 300 of FIG. 3; the example system 410 of FIG. 4; and the example computer-readable storage device 502 of FIG. 5) to confer individual and/or synergistic advantages upon such embodiments.

E1. Scenarios

A first aspect that may vary among embodiments of these techniques relates to the scenarios wherein such techniques may be utilized.

As a first variation of this first aspect, the techniques presented herein may be used with many types of travelers 104, including vehicles such as automobiles, motorcycles, trucks, trains, buses, watercraft, aircraft, drones, and spacecraft; pedestrians, such as individuals in a crowd; and migratory wildlife. The techniques may also be utilized to estimate traveler volume 104 in many environments, such as a roadway, highway, parking lot, sidewalk, dirt or grass path, waterway, airspace, and an enclosed structure such as a shopping mall.

As a second variation of this first aspect, the probes 106 among such travelers 104 may comprise, e.g., travelers 104 who are carrying a particular device that reports probe speed, or travelers 104 that are visually recognizable and therefore trackable (e.g., an aerial vehicle, such as a drone, may be capable of tracking the transit pattern of a distinctive individual or vehicle over time).

As a third variation of this first aspect, a transit queue 110 may form in an area 102 of travelers 104 for a variety of reasons, such as a vehicular accident; an excess of traveler volume that exceeds the capacity of the area 102, or of an adjacent area 102 to which the area 102 provides entry; a regulatory stop, such as the collection of tolls by a toll booth; an obstruction of the area 102, such as the presence of debris, wildlife, or weather patterns that slow or prevent transit through the area 102; or congregation of travelers 104 in an area that slows the transit of other travelers 104. Many such scenarios may be devised wherein the techniques provided herein may be advantageously utilized.

E2. Area Identification and Evaluation

A second aspect that may vary among embodiments of the techniques presented herein involves the manner of identifying and evaluating an area 102 in order to collect information for transit volume estimates 218 of the area 102.

As a first variation of this second aspect, an area 102 may be defined according to a fixed boundary, such as a span of road between two distance markers, or a region defined by a set of global positioning service (GPS) coordinates.

As a second variation of this second aspect, the area 102 may be identified according to the probe speed of the respective probes 106 in the area 102. For example, the transit service 114 may identify a queue start point of the transit queue 110 in the area 102, e.g., as a start location where the probe speeds of the probes 106 fall below an average probe speed for the area 102, and a queue end point for the transit queue 110, e.g., as an end location where the probe speeds of the probes 106 are restored to an average probe speed for the area 102.

As a third variation of this second aspect, the transit queue length 204 of the transit queue 110 may be evaluated in a number of ways. As a first such example, the transit queue length 204 may be determined, e.g., as a geographic length between the start location and the end location of the transit queue 110 (e.g., a comparison of the global positioning system (GPS) coordinates spanned by the transit queue 110). As a second such example, the length be identified as the length of respective segments of an area 102, and the number of segments that the traffic queue 110 spans in the area 102 (e.g., the number of distance markers along a road that are spanned by the transit queue 110).

As a fourth variation of this second aspect, the traveler length 206 of travelers 104 in the transit queue 110 may be determined in various ways. As a first such example, traveler length 206 may simply be selected as a standardized average; e.g., the length of an average automobile in the United States is 4.8 meters, and driving distance between vehicles in slow-moving traffic is typically about two meters, leading to an average traveler length 206 of 6.8 meters.

Figure 6:
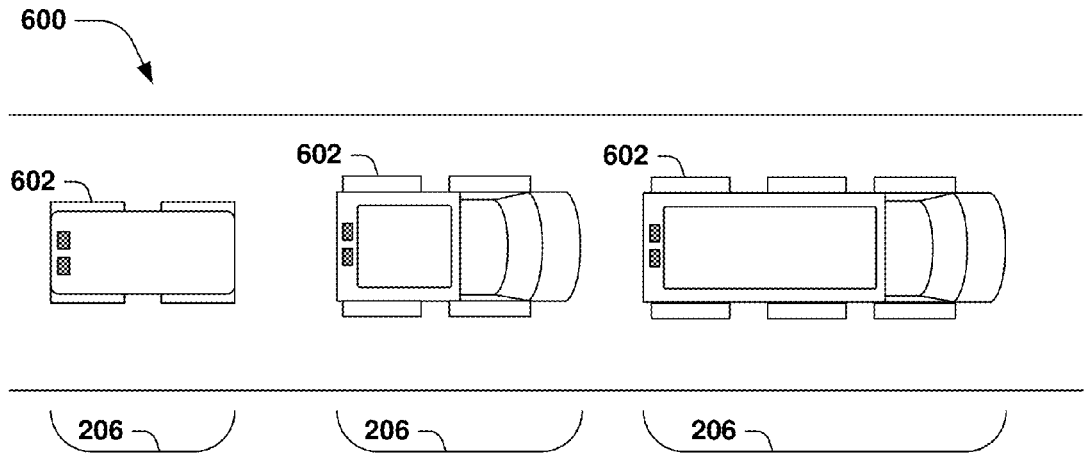
FIG. 6 is an illustration of an example scenario featuring a first technique for estimating a traveler length of travelers according to a traveler type, in accordance with the techniques presented herein.

FIG. 6 presents an illustration of an example scenario 600 featuring a second technique for estimating traveler length 206 among travelers 104. In this example scenario 600, respective travelers 104 are of a traveler type 602; e.g., an compact automobile, a mid-size utility vehicle, and a six-wheel bus. The respective traveler types 602 may each be associated with a typical traveler length 206, which may be factored into the estimates of traveler length 206 that inform the determination of the probe ratio 216. As a first such example, the demographics of the area 102 may be estimated (e.g., a local population comprises 70% compact automobiles, 25% mid-size utility vehicles, and 5% six-wheel buses), and the traveler lengths 206 may be extrapolated from such demographics. As a second such example, respective probes 106 may also transmit to the transit service 104 a traveler type 602, such as the make and model of the vehicle, and the demographics of the probes 106 may be proportionally extrapolated as the demographics of the travelers 104. As a third such example, a machine vision technique may be utilized to visually classify the traveler types 602 of travelers 104 in an area 102 or a representative sample thereof, and proportions of traveler types 602 of the classified travelers 104 may be extrapolated to the travelers 104 in the area 102.

Figure 7:
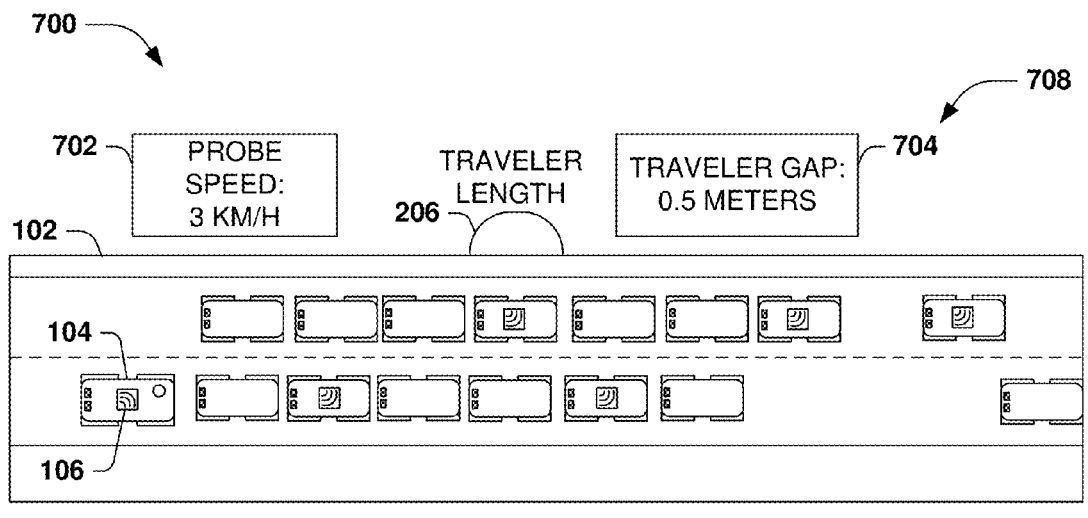
FIG. 7 is an illustration of an example scenario featuring a second technique for estimating a traveler length of travelers according to a traveler type, in accordance with the techniques presented herein.
Figure 7:
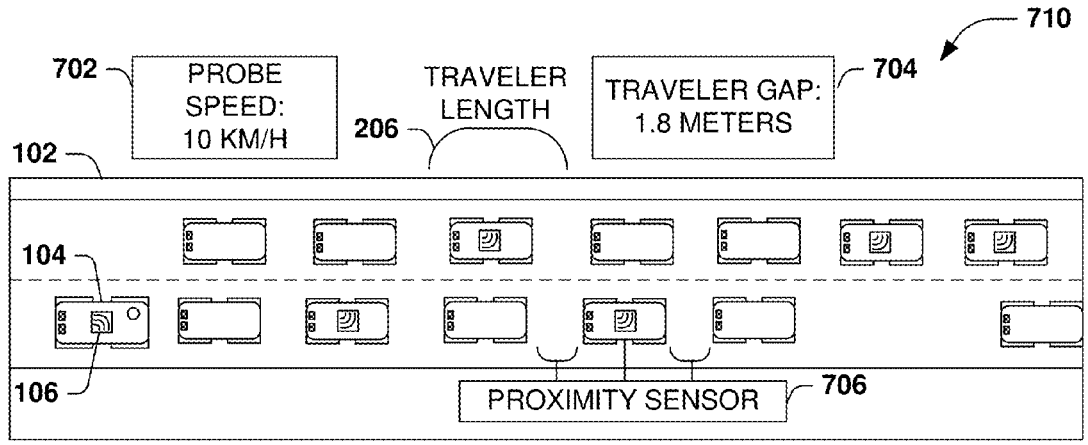

FIG. 7 presents an illustration of an example scenario 700 featuring a third technique for estimating traveler length 206 among travelers 104. In this example scenario 700, traveler length 206 is also, partly or wholly, determined according to probe speeds 702 of probes 106, which may partly determine a traveler gap 704 between a probe 106 and nearby travelers 104 in the transit queue 110. For example, in a first such scenario 708, travelers 104 are traveling at a very slow probe speed 702 and may maintain a very small traveler gap 704 (e.g., "bumper-to-bumper" "traffic"); while in a second such scenario 710, travelers 104 may be traveling at a reduced but moderate speed (e.g., "stop-and-go" traffic), and may maintain a marginally larger traveler gap 704. The traveler gap 704 may be factored into the estimation of traveler length 206 as a property of probe speeds 702. Alternatively or additionally, the traveler gap 704 may be directly measured and/or reported; e.g., a proximity sensor 706 of a probe 106 may detect the traveler gap 704 with respect to a leading traveler 104 and/or a following traveler 104, and may report the traveler gap 704 to the transit service 104 along with the probe speed.

As a fifth variation of this second aspect, the detection of a probe ingress rate 210 and/or probe egress 212 with respect to the transit queue 110 may be determined in a variety of ways. As a first such example, probe ingress rate 210 and/or probe egress 212 may be determined with respect to probe speeds 702; e.g., probes 106 may be determined as entering the transit queue 110 when a probe speed 702 falls below a typical probe speed 702 for the area 102, and/or as entering the transit queue 110 when the probe speed 702 is restored to a typical probe speed 702 for the area 102. As a second such example, probes 106 may be detected as entering and/or exiting the transit queue 110 by comparing the locations of the probes 106 with the area 102 identified as the transit queue 110.

Figure 8:
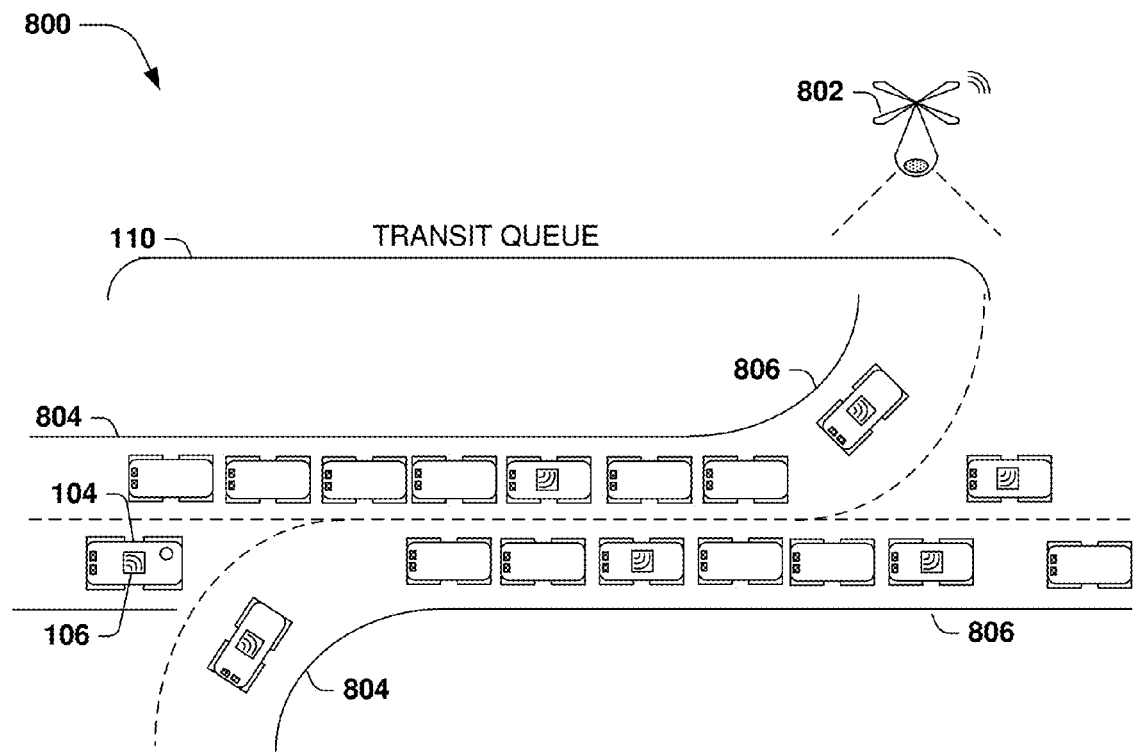
FIG. 8 is an illustration of an example scenario featuring various techniques for estimating a queue length of a transit queue, in accordance with the techniques presented herein.

FIG. 8 presents an illustration of a third example of this fifth variation of this second aspect, wherein probes 106 are determined as entering and/or exiting the transit queue 110 according to ingress points 804 and/or egress points 804 of the transit queue 110. In this example scenario 800, the transit queue 110 may be detected in a particular area 102 (e.g., through evaluation of the area 102 by an aerial vehicle 802 such as a drone), and drones 106 may be detected as entering and/or leaving the transit queue 110. More particularly, along the span of road upon which the transit queue 110 occurs, a number of ingress points 804 and egress points 806 may be identified where, respectively, travelers 104 enter and exit the transit queue 110. Such ingress points 804 and egress points 806 may include, e.g., the location along the span of the road where travelers 104 begin to accumulate, and/or where travelers 104 are able to resume a typical speed for the area 102. Additional ingress points 804 and egress points 806 may include locations where travelers may enter and/or exit the transit queue 110 midway, e.g., an entrance ramp that joins in the middle of the transit queue 110. The ingress and/or egress of probes 106 may be determined by identifying such ingress points 804 and egress points 806, and monitoring the locations of the probes 106 to detect when a probe 106 crosses into and/or out of the transit queue 110. These and other details of the area 102, the travelers 104 and probes 106 therein, and the transit queue 110 may be detected and utilized in accordance with the techniques presented herein.

E3. Calculation of Probe Ratios

A third aspect that may vary among embodiments of the techniques presented herein involves the manner of calculating the probe ratios 216 according to the collected information about the area 102, the probes 106, and the transit queue 110.

As a first variation of this third aspect, an area 102 may be partitioned into at least two segments, such as at least two lanes of a path such as a road. The probe locations of the respective probes 106 may be associated with a selected segment of the at least two segments of the area 102, and transit volume of the transit queue 110 may be identified for the selected segment using the count of the probes 106 associated each selected segment (e.g., the number of probes 106 in each lane of a road). As a first such example, a first segment may be identified as a first subset of probes 106 reporting a first average probe speed, and a second segment may be identified as a second subset of probes 106 reporting a second average probe speed that is different from the first average probe speed of the first segment. As a second such example, a first segment may be identified that represents a first transit area type (e.g., a high-occupancy vehicle lane or restricted-access lane of a road), and a second segment representing a second transit area type that is different from the first transit area type of the first segment (e.g., a general-use lane of the same road). As a third such example, the area 102 may comprise at least two ingress points and at least two egress points (e.g., various entrance and exit ramps along a highway), and the area 102 may be partitioned into segments respectively representing a span of the area 102 between a selected ingress point and a selected egress point.

Figure 9:
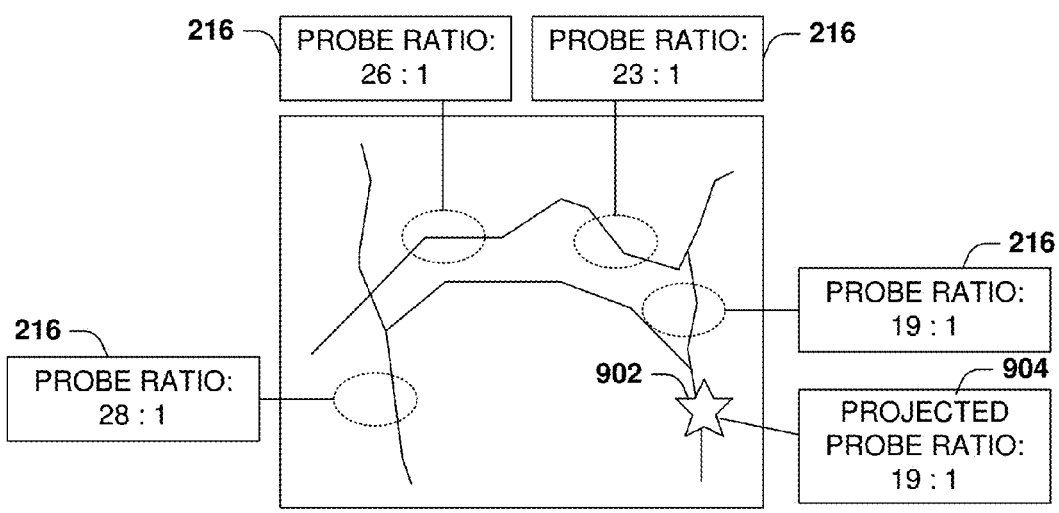
FIG. 9 is an illustration of an example scenario featuring an estimation of probe ratios in different areas of a region, in accordance with the techniques presented herein.

FIG. 9 presents an illustration of an example scenario 900 featuring one such variation of the techniques presented herein, wherein different probe ratios 216 may be calculated for different areas 102 within a region. For example, different segments of a road network may be construed as representing different populations of a region, which may exhibit different probe ratios 216 (e.g., a first area 102 may have a high population of users who utilize mobile devices featuring a probe application, while a second area 102 may have a lower population of such users). Different probe ratios 216 may therefore be determined for different locations, and a transit volume for a particular area 902 may be determined using a projected probe ratio 904, e.g., according to the closest area(s) 102 for which a probe ratio 216 has been determined.

Alternatively or additionally, the calculation of probe ratios 216 may be identified as an average of several transit queues 110. For example, an incidental aggregation of probes 106 in a particular area 102 (e.g., a large number of individuals from a school or organization who choose to enroll in a traffic monitoring system) may lead to a local overestimation of transit volume, but such overestimation may be reduced by averaging the probe ratios 216 over several transit queues 110 in a particular area. Accordingly, probe ratios 216 may be identified for each of at least two transit queues 110 in an area 102, and the probe ratios of the transit queues 110 may be averaged into a regional probe ratio for the area.

As a second variation of this third aspect, the calculation of the probe ratio 216 from such collected information may be performed according to many mathematical techniques. As one such technique, the following mathematical formula may be used:

$$R = \frac{\frac{Q}{L}}{I - E},$$

wherein:

R represents the probe ratio 216 of travelers 104 to probes 106;

Q represents the transit queue length change 208 of the transit queue 110;

L represents the traveler length 206;

I represents the probe ingress rate 210; and

E represents the probe egress rate 212.

As a third variation of this third aspect, many other sources of information may be collected and used to inform the determination of the probe ratio 216, and/or may be extrapolated from the probe ratio 216. As a first such example, a queue duration may be estimated for the transit queue 110. As a second such example, a queue severity may be estimated for the transit queue 110, according to a probe speed differential between an average probe speed 702 of the probes 106 and a typical probe speed 702 for travelers 104 in the area 102. As a third such example, respective transit queues 110 may be associated with a queue type selected from a queue type set (e.g., transit queues 110 caused by various factors, such as a vehicular accident, construction, or excessive traveler volume), and a transit queue modeler may further classify the transit queue 110 as a queue type selected from the queue type set. Many such calculations and/or data points may be utilized in and/or derived from the evaluation of the transit queue 110, and the estimation of the probe ratio 210 and/or the transit volume, identified therefor in accordance with the techniques presented herein.

E4. Uses of Transit Volume Estimation

A fourth aspect that may vary among embodiments of the techniques presented herein involves the uses of the transit volume estimation 218, e.g., by the travelers 104 and probes 106 in the area 102, and/or a transit service 114 that is responsible for managing transit volume for the area 102.

As a first variation of this second aspect, the transit volume estimate 216 of travelers 104 in an area 102 may be observed and calculated as many types of measurements, such as a count of travelers; a density of travelers in an area; a size or mass of the collection of travelers in the area; and/or a change or trend in the number of travelers in the area 102. Additionally, civic planners may utilize transit volume estimates 216 to allocate resources, such as the expansion of roads and/or the development of new roads in a municipal road network.

As a second variation of this fourth aspect, a traveler 104 may be embarking on travel including a route through the area 104 to a destination, and having a destination arrival estimate. The transit volume estimation may be utilized to notify the user of the transit queue 110 in the area 102. As a first such example, the transit volume estimation 216 may inform an identification of an alternative route to the destination that avoids the transit queue 110, and the user may be notified of the alternative route to the destination. Alternatively, an autonomous vehicle may automatically select the alternative route to avoid the transit queue 110. As a second such example, the route of the user may be associated with a destination arrival estimate, and the transit volume estimation 216 may enable an estimation of an adjusted destination arrival estimate according to the queue length change of the transit queue 110, and a device may inform the user of the adjusted destination arrival estimate.

As a third variation of this fourth aspect, a transit service 114 may utilize the transit volume estimate 216 to control transit through the area 102 and/or several areas 102 of a region, e.g., by controlling transit control devices in various areas 102 to redistribute transit volume.

Figure 10:
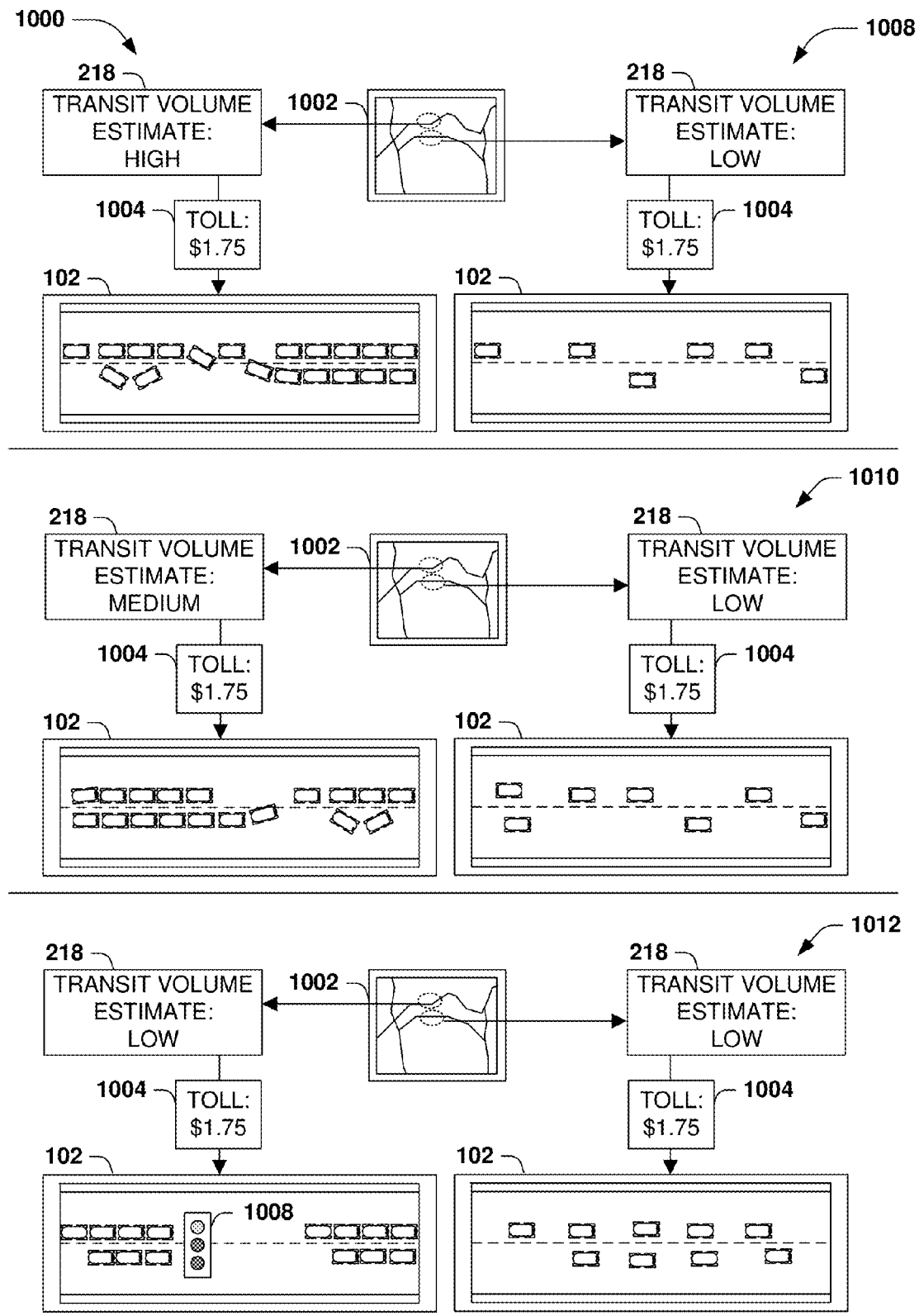
FIG. 10 is an illustration of an example scenario featuring a control of transit volume in an area using transit control devices, in accordance with the techniques presented herein.

FIG. 10 is an illustration of an example scenario 1000 featuring the use of several such variations by a transit service 114 to control adjust vehicle transit through various areas 102 of a region 902. In this example scenario 1000, the transit service 114 may impose a transit restriction through a transit control, in proportion with the transit volume of travelers 104 in the areas 102, which may persuade travelers 104 to choose routes and driving behaviors that redistribute the transit volume 104 throughout the region 902. At a first time 1008, the transit service 114 may generate estimates of vehicle transit in various areas 102, and a transit toll 1004 is assessed to each traveler 104 in transit in the area 102. Transit volume estimates 218 may indicate that the first area 102 is exhibiting high transit volume, while a second area 102 exhibits comparatively few travelers 104 and comparatively light transit volume. In order to reduce this disparity, at a second time 1010, the transit tolls 1004 for the respective areas 102 may be adjusted (e.g., increasing the toll 1004 for the first area 102 while reducing the toll 1004 for the second area 102) in order to persuade travelers 104 to choose a detour through the second area 102. The transit service 114 may transmit a signal to transit control devices that collect the tolls 1004 from the travelers 104, and may therefore instruct the transit control devices to adjust the tolls 1004 in proportion with the vehicle transit in each area 102. Transit volume estimates 218 may continue to be collected, and the adjustment of the tolls 1004 may reveal modest, but not adequate, redistribution of transit volume. Accordingly, at a third time 1012, a second transit control device 1006 may be adjusted, e.g., a stoplight that periodically restricts the entry of travelers 104 to the first area 102, and thereby reduces transit volume therein. Additionally, to the transit service 114 may recommend to the travelers 104 a detour area exit, which may provide an alternative route to traveling through the first area 102 having high transit volume. In this manner, the transit service 114 may utilize transit controls to adjust the transit volume through various areas 102 of the region 1002 in accordance with the techniques presented herein.

F. Computing Environment

Figure 11:
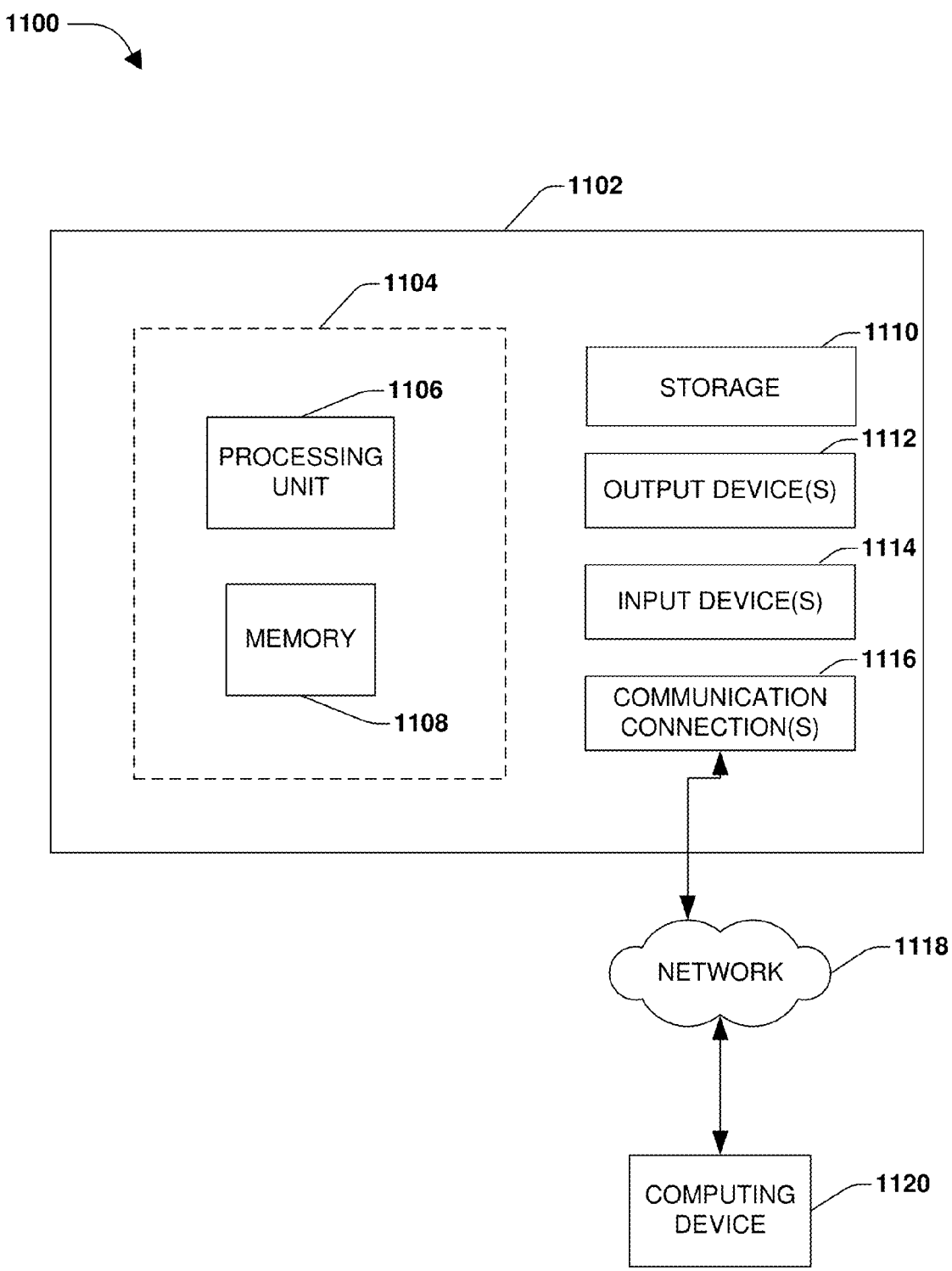
FIG. 11 is an illustration of an example computing environment wherein one or more of the provisions set forth herein may be implemented.

FIG. 11 and the following discussion provide a brief, general description of a suitable computing environment to implement embodiments of one or more of the provisions set forth herein. The operating environment of FIG. 11 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 11 illustrates an example of a system 1100 comprising a computing device 1102 configured to implement one or more embodiments provided herein. In one configuration, computing device 1102 includes at least one processing unit 1106 and memory 1108. Depending on the exact configuration and type of computing device, memory 1108 may be volatile (such as RAM, for example), non-volatile (such as ROM, flash memory, etc., for example) or some combination of the two. This configuration is illustrated in FIG. 11 by dashed line 1104.

In other embodiments, device 1102 may include additional features and/or functionality. For example, device 1102 may also include additional storage (e.g., removable and/or non-removable) including, but not limited to, magnetic storage, optical storage, and the like. Such additional storage is illustrated in FIG. 11 by storage 1110. In one embodiment, computer readable instructions to implement one or more embodiments provided herein may be in storage 1110. Storage 1110 may also store other computer readable instructions to implement an operating system, an application program, and the like. Computer readable instructions may be loaded in memory 1108 for execution by processing unit 1106, for example.

The term "computer readable media" as used herein includes computer storage media. Computer storage media includes volatile and nonvolatile, removable and non-removable media implemented in any method or technology for storage of information such as computer readable instructions or other data. Memory 1108 and storage 1110 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 1102. Any such computer storage media may be part of device 1102.

Device 1102 may also include communication connection(s) 1116 that allows device 1102 to communicate with other devices. Communication connection(s) 1116 may include, but is not limited to, a modem, a Network Interface Card (NIC), an integrated network interface, a radio frequency transmitter/receiver, an infrared port, a USB connection, or other interfaces for connecting computing device 1102 to other computing devices. Communication connection(s) 1116 may include a wired connection or a wireless connection. Communication connection(s) 1116 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 1102 may include input device(s) 1114 such as keyboard, mouse, pen, voice input device, touch input device, infrared cameras, video input devices, and/or any other input device. Output device(s) 1112 such as one or more displays, speakers, printers, and/or any other output device may also be included in device 1102. Input device(s) 1114 and output device(s) 1112 may be connected to device 1102 via a wired connection, wireless connection, or any combination thereof. In one embodiment, an input device or an output device from another computing device may be used as input device(s) 1114 or output device(s) 1112 for computing device 1102.

Components of computing device 1102 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 1102 may be interconnected by a network. For example, memory 1108 may be comprised of multiple physical memory units located in different physical locations interconnected by a network.

Those skilled in the art will realize that storage devices utilized to store computer readable instructions may be distributed across a network. For example, a computing device 1120 accessible via network 1118 may store computer readable instructions to implement one or more embodiments provided herein. Computing device 1102 may access computing device 1120 and download a part or all of the computer readable instructions for execution. Alternatively, computing device 1102 may download pieces of the computer readable instructions, as needed, or some instructions may be executed at computing device 1102 and some at computing device 1120.

G. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "example" is used herein to mean serving as an example, instance, or illustration. Any aspect or design described herein as "example" is not necessarily to be construed as advantageous over other aspects or designs. Rather, use of the word example is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method of estimating transit volume in an area, the method involving a device having a processor and comprising:
    executing, on the processor, instructions that cause the device to:
        monitor a probe speed of respective probes in the area to detect a transit queue;
        from the probe speeds of the probes:
            estimate a queue length change of the transit queue;
            estimate a probe rate change of probes in the transit queue;
            from the queue length change and the probe rate change, identify a probe ratio among travelers of the transit queue; and
            using a count of the probes and the probe ratio, identify the transit volume of the transit queue.

2. The method of claim 1, wherein executing the instructions further causes the device to, according to the probe speed of the respective probes in the area:
    identify a start location of the transit queue in the area; and
    identify an end location the transit queue in the area.

3. The method of claim 1, wherein estimating the queue length change further comprises:
    estimating a geographic length of the queue;
    estimating an average traveler length of travelers in the transit queue; and
    dividing the geographic length of the queue by the average traveler length.

4. The method of claim 3, wherein estimating the average traveler length further comprises:
    estimating an average probe speed of travelers in the transit queue; and
    estimating the average traveler length proportionally with the average probe speed of travelers in the transit queue.

5. The method of claim 1, wherein executing the instructions further causes the device to identify, according to the probe speed of the respective probes in the area:
    an ingress of the probe to the transit queue indicated by a reduction in the probe speed below a typical probe speed for the area; and
    an egress of the probe from the transit queue indicated by a restoration of the typical probe speed for the area.

6. The method of claim 1, wherein:
    executing the instructions further causes the device to:
        partition the area into at least two segments, and
        associate a probe location of the respective probes with a selected segment of the at least two segments of the area; and
    identifying the transit volume further comprises: for a selected segment, identifying the transit volume of the transit queue for the selected segment using the count of the probes associated with the selected segment.

7. The method of claim 6, wherein:
    the area comprises a path having at least two lanes; and
    partitioning the area further comprises: partitioning the path into at least two segments respectively representing one of the at least two lanes.

8. The method of claim 6, wherein partitioning the area further comprises:
    partitioning the area into:
        a first segment including a first subset of probes reporting a first average probe speed; and
        a second segment including a second subset of probes reporting a second average probe speed that is different from the first average probe speed of the first segment.

9. The method of claim 6, wherein partitioning the area further comprises:
    partitioning the area into:
        a first segment representing a first transit area type; and
        a second segment representing a second transit area type that is different from the first transit area type of the first segment.

10. The method of claim 6, wherein:
    the area further comprises at least two ingress points and at least two egress points; and partitioning the area further comprises: partitioning the area into segments respectively representing a span of the area between a selected ingress point and a selected egress point.

11. A server that estimates a transit volume in an area having, the server comprising:
a processor;
a probe communicator that receives, from respective probes in the area, a report of a probe speed; and
a memory storing instructions that, when executed by the processor, provide a system comprising:
   a transit queue detector that, from the probe speeds of the probes, identifies a transit queue;
   a transit queue modeler that, from the probe speeds of the probes:
      estimates a queue length change of the transit queue;
      estimates a probe rate change of probes in the transit queue; and
   a transit volume estimator that:
      from the queue length change and the probe rate change, identifies a probe ratio among travelers of the transit queue; and
      using a count of the probes and the probe ratio, identifies the transit volume of the transit queue.

12. The server of claim 11, wherein identifying the transit volume further comprises:
identifying a probe ratio for each of at least two transit queues in an area; and
averaging the probe ratios for the at last two transit queues to identify a regional probe ratio for the area.

13. The server of claim 11, wherein the transit queue modeler further estimates a queue length change rate of the queue length of the transit queue.

14. The server of claim 11, wherein the transit queue modeler further estimates a queue duration of the transit queue.

15. The server of claim 11, wherein the transit queue modeler further estimates a queue severity of the transit queue according to a probe speed differential between an average probe speed of the probes and a typical probe speed for travelers in the area.

16. The server of claim 11, wherein:
respective transit queues are associated with a queue type selected from a queue type set; and
the transit queue modeler further classifies the transit queue as a queue type selected from the queue type set.

17. A nontransitory computer-readable medium storing instructions that, when executed by a processor of a device, cause the device to estimate a transit volume of a transit queue in an area, by:
monitoring a probe speed of respective probes in the area to detect a transit queue;
from the probe speeds of the probes:
   estimating a queue length change of the transit queue;
   estimating a probe rate change of probes in the transit queue;
from the queue length change and the probe rate change, identifying a probe ratio among travelers of the transit queue; and
using a count of the probes and the probe ratio, identifying the transit volume of the transit queue.

18. The nontransitory computer-readable medium of claim 17, wherein:
a user of a selected traveler is associated with a route through the area to a destination, and having a destination arrival estimate; and
executing the instructions further causes the device to notify the user of the transit queue in the area.

19. The nontransitory computer-readable medium of claim 18, wherein executing the instructions further causes the device to:
identify an alternative route to the destination that avoids the transit queue; and
notify the user of the alternative route to the destination.

20. The nontransitory computer-readable medium of claim 18, wherein:
the route of the user is associated with a destination arrival estimate; and
executing the instructions further causes the device to:
   identify an adjusted destination arrival estimate according to the queue length change of the transit queue; and
   notify the user of the adjusted destination arrival estimate.

* * * * *